(12) United States Patent
Barth

(10) Patent No.: US 7,147,849 B2
(45) Date of Patent: Dec. 12, 2006

(54) PHARMACEUTICAL FORMULATION

(75) Inventor: Stefan Barth, Roetgen (DE)

(73) Assignee: Bitop AG, Witten (DE)

(*) Notice: Subject to any disclaimer, the term of this patent is extended or adjusted under 35 U.S.C. 154(b) by 499 days.

(21) Appl. No.: 10/429,256

(22) Filed: May 5, 2003

(65) Prior Publication Data

US 2004/0071691 A1    Apr. 15, 2004

Related U.S. Application Data

(63) Continuation of application No. 09/926,749, filed as application No. PCT/EP00/05309 on Jun. 8, 2000, now abandoned.

(30) Foreign Application Priority Data

Jun. 12, 1999  (DE) ................................ 199 26 877
May 17, 2000  (DE) ................................ 100 24 301

(51) Int. Cl.
*A61K 39/395*    (2006.01)
*A61K 47/00*    (2006.01)

(52) U.S. Cl. .............. 424/130.1; 424/134.1; 424/136.1; 424/178.1; 424/182.1; 424/183.1; 424/278.1; 530/387.1; 530/391.1; 530/391.7

(58) Field of Classification Search ............ 424/130.1, 424/136.1, 178.1, 182.1, 183.1, 278.1, 134.1; 530/387.1, 391.1, 391.7
See application file for complete search history.

(56) References Cited

U.S. PATENT DOCUMENTS

| | | | |
|---|---|---|---|
| 5,512,282 A * | 4/1996 | Krivan et al. ............ 424/169.1 |
| 5,569,457 A | 10/1996 | Shug et al. |
| 5,789,414 A * | 8/1998 | Lapidot et al. ............ 514/256 |
| 5,869,050 A | 2/1999 | de Boer et al. |
| 6,024,955 A * | 2/2000 | Asano et al. ............ 424/130.1 |
| 6,313,102 B1 * | 11/2001 | Colaco et al. ................ 514/53 |

FOREIGN PATENT DOCUMENTS

| | | |
|---|---|---|
| DE | 4244580 A1 | 7/1994 |
| DE | 19933466 A1 | 1/2000 |
| WO | WO 95/01154 | 1/1995 |
| WO | WO 97/04801 | 2/1997 |
| WO | WO 97/38685 | 10/1997 |
| WO | PCT/EP00/05309 | 6/2001 |

OTHER PUBLICATIONS

Barth et al (Applied & Environmental Microbiology 66:1572-1579, Apr. 2000).*
Baluna et al (Immunopharmacology 37:117-132, 1997).*
Lippert et al. Appl. Microbiol. Biotech. 37: 61-65, 1994.*
Da Costa et al. Advances in Biochemical Engineering/Biotechnology 61:117-153, 1998.*
Audran et al., "*Enhanced Immunogenicity of Microencapsulated Tetanus Toxiod with Stabilizing Agents*", XP-000990406, Pharmaceutical Research., vol. 15., No. 7, (1998), pp. 111-1116.
Sauer et al., "*Ectoine—Biotechnische Produktion und Mogliche Anwendungsbereiche*", GIT Fachz Lab. (Oct. 1995), pp. 892-896.
da Costa et al., "*An Overview of the Role an Diversity of Compatible Solutes in Bacteria and Archaea*", XP-002099622, Advances in Biochemical Engineering/Biotechnology, vol. 61, Th. Scheper, (Jul. 1997), pp. 117-153.

* cited by examiner

*Primary Examiner*—Mary E. Mosher
(74) *Attorney, Agent, or Firm*—Jacobson Holman PLLC

(57) ABSTRACT

A pharmaceutical formulation containing at least one protein-containing substance and at least one substance selected from the group of compatible solutes.

5 Claims, 1 Drawing Sheet

PHARMACEUTICAL FORMULATION

This is a continuation of application Ser. No. 09/926,749, filed Dec. 12, 2001, which is a 371 of PCT/EP00/05309, filed Jun. 8, 2000.

The present invention relates to a pharmaceutical formulation and its use.

EP-A-0 553 884 describes purified tetrahydropyridine derivatives and pharmaceutical formulations containing these derivatives. They are suitable for protecting the DNA from damage by DNA-binding active substances, chemical carcinogens and mutagens and radiation damage.

Surprisingly, it has now been found that compatible solutes are suitable for enhancing the effectiveness of protein-containing substances. Therefore, the invention relates to a pharmaceutical formulation containing at least one protein-containing substance and at least one substance selected from the group of compatible solutes.

Figure 1:
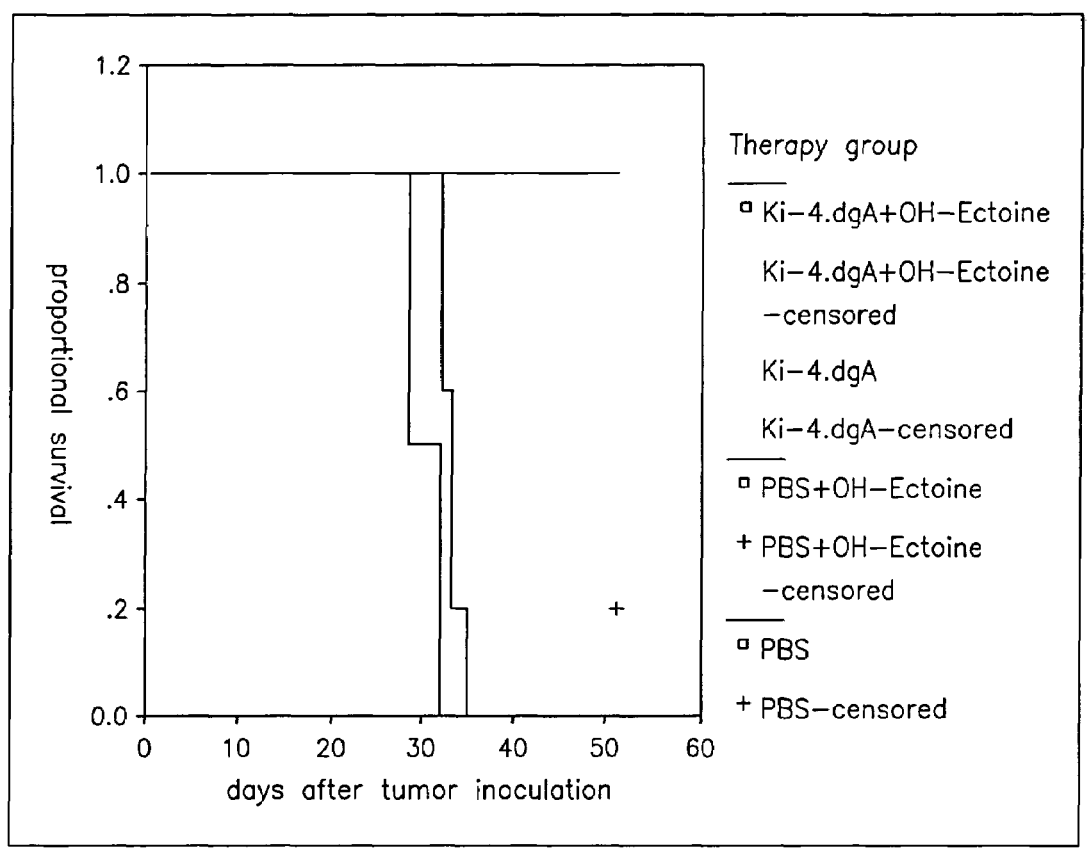
FIG. 1 is a graph showing test results in a Kaplan-Meier representation.

The compatible solute class of substances includes sugars and polyols (e.g., trehalose, glycerol, glycosylglycerol, beta-mannosylglycerate, beta-mannosylglyceramide, di-myo-inositol phosphate, 1,1-diglycerol phosphate, dimannosyl-diinositol phosphate, cyclic 2,3-diphosphoglycerate), natural amino acids (e.g., alanine, proline, glutamine), derivatives of amino acids (e.g., N-acetylated diamino acids, N-acetyllysine, glutamine-1-amide, taurine), betaines (e.g., glycine betaine, proline betaine, glutamate betaine, choline, choline-O-sulfate, carnitine, arsenobetaine, crotonobetaine, dimethylsulfonio acetate, dimethylsulfonio propionate, homobetaine, trimethylamine-N-oxide) and ectoines (L-ectoine, S,S-β-hydroxyectoine).

Preferred substances from the group of compatible solutes are betaines and ectoines.

The protein-containing substance is preferably selected from natural, synthetic or recombinant polypeptides, natural, synthetic or recombinant proteins, protein-containing antigens, protein conjugates, protein-containing cell fragments, protein-containing cell membranes, and whole cells.

Preferably, the protein-containing substance is an antibody, an antibody fragment, a recombinant mono- or higher valent antibody, a recombinant mono- or higher valent antibody fragment, a bispecific antibody, a diabody or an immunotoxin derived therefrom.

The pharmaceutical formulation according to the invention is particularly suitable for the treatment of tumor diseases, autoimmune diseases, chronic inflammations, allergies, bacterial and viral infections. In addition, it reduces cytotoxic activities occurring in the course of the treatment, especially the "vascular leak syndrome" (VLS). In the latter syndrome, a direct damage to endothelial cells results in a loss of albumin from the intracellular space into the extracellular space; this results in an increasing accumulation of interstitial fluid and consequently in a gain of weight with formation, above all, of edema, hypotensions and tachycardias.

The invention also relates to the use of substances selected from the group of compatible solutes for enhancing the effectiveness of protein-containing substances.

The effectiveness of the pharmaceutical formulation according to the invention is further illustrated by the following Example:

Use of a Pharmaceutical Formulation Consisting of an Anti-CD30 Immunotoxin and S,S-β-hydroxyectoine in SCID Mice with Disseminatedly Growing Human L540Cy Tumors.

1. Methods $1 \times 10^7$ L540Cy cells derived from Hodgkin's lymphoma were injected intravenously into four-week old female SCID mice. One day later, the animals were treated intravenously with the chemically coupled anti-CD30 immunotoxin Ki-4.dgA (50 μg) with and without 1 M S,S-β-hydroxyectoine; in parallel experiments, control animals were treated with PBS buffer with and without 1 M S,S-βhydroxyectoine.

The immunotoxin employed is currently being tested in a clinical phase I study in the Medizinische Klinik I with patients suffering from Hodgkin's lymphoma who could not be cured by conventional therapies or have had a relapse. The immunotoxin available under GMP conditions was employed at a dose of 50 μg in the mice. As the maximum tolerable dose, a quantity of 48 μg was documented with this immunotoxin in SCID mice.

2. Results

The preliminary results of this experiment can be seen from the appended graph in a Kaplan-Meier representation. All control animals developed disseminatedly growing tumors within 35 days. These animals were sacrificed, and their tumor infestation documented: macroscopically visible tumors developed in the lymph nodes, kidneys, ovaries, thymus, chewing muscles and brain.

For the 5 animals of the PBS group without and the 2 animals of the PBS group with S,S-β-hydroxyectoine, average survival rates of 33.0 (±0.55) days and 30.0 (±2) days, respectively, were calculated according to Kaplan-Meier.

Four of the five animals treated with Ki-4.dgA died within a day from the administered dose, and the fifth animal first suffered from a high loss of weight (about 3 g), but recovered within 5 days. As compared with the control animals, no sign of tumor development could be detected in the observation period of as yet 51 days.

None of the four animals treated with Ki-4.dgA+S,S-β-hydroxyectoine died within the observation period and did not show any signs of tumor development either.

The difference between the groups "PBS without or with S,S-β-hydroxyectoine" and "Ki-4.dgA with S,S-β-hydroxyectoine" is highly significant (P=0.0046) and significant (P=0.0177) statistically. Groups "Ki-4.dgA without and with S,S-β-hydroxyectoine" are significantly different (P=0.0237). In addition, a difference according to tendency can be seen between the groups "PBS without and with S,S-β-hydroxyectoine" (P=0.0715), which could indicate a faster tumor development in animals treated with S,S-β-hydroxyectoine.

The invention claimed is:

1. A method of reducing vascular leak syndrome caused by administration of a protein-containing substance to treat disease comprising the step of administering the protein-containing substance together with ectoine to a person in need thereof.

2. The method of claim 1 wherein the ectoine is L-ectoine or S,S-β hydroxyectoine.

3. The method of claim 1 wherein the protein-containing substance is selected from the group consisting of natural, synthetic and recombinant polypeptides, natural, synthetic and recombinant proteins, protein-containing antigens, protein conjugates, protein-containing cell fragments, protein-containing cell membranes, and whole cells.

4. In a therapeutic composition for humans comprising a therapeutically effective antibody, antibody fragment, or toxic conjugate derived therefrom, the improvement wherein the composition further comprises ectoine.

5. In therapeutic method comprising administering a therapeutically effective antibody, antibody fragment, or toxic conjugate derived therefrom to a person in need thereof, the improvement comprising administering the therapeutcally effective antibody, antibody fragment, or immunotoxin in combination with ectoine.

* * * * *